(12) United States Patent
Shinno

(10) Patent No.: US 8,396,184 B2
(45) Date of Patent: Mar. 12, 2013

(54) X-RAY CT SYSTEM AND CONTROL METHOD FOR SAME

(75) Inventor: Toshiyuki Shinno, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 265 days.

(21) Appl. No.: 12/957,646

(22) Filed: Dec. 1, 2010

(65) Prior Publication Data

US 2011/0150173 A1   Jun. 23, 2011

(30) Foreign Application Priority Data

Dec. 17, 2009   (JP) ................................. 2009-286444

(51) Int. Cl.
*A61B 5/00* (2006.01)

(52) U.S. Cl. ........................................................... 378/5

(58) Field of Classification Search ................ 378/4–21
See application file for complete search history.

(56) References Cited

FOREIGN PATENT DOCUMENTS

| JP | 2001-59872 | 3/2001 |
|---|---|---|
| JP | 2001-286459 | 10/2001 |
| JP | 2002-177261 | 6/2002 |
| JP | 2005-80749 | 3/2005 |
| JP | 2005-230547 | 9/2005 |

OTHER PUBLICATIONS

Chinese Office Action issued Feb. 24, 2012, in Patent Application No. 201010593214.6.

*Primary Examiner* — Courtney Thomas
(74) *Attorney, Agent, or Firm* — Oblon, Spivak, McClelland, Maier & Neustadt, L.L.P.

(57) ABSTRACT

An X-ray CT system of an embodiment includes the following. An imaging region data acquisition part is configured to acquire a first imaging region and a second imaging region that have different widths from each other in the body axial direction based on a scanogram as imaging regions for performing scan imaging. An irradiation field control part is configured to obtain irradiation fields for the first and the second imaging regions, and control an irradiation field regulating part corresponding to the relative positions by a moving part so as to realize the irradiation fields obtained for each the imaging region. An X-ray control part is configured to control an X-ray generating part corresponding to the relative positions by the moving part so as to irradiate X-rays to the first and the second imaging regions for the scan imaging.

11 Claims, 7 Drawing Sheets

X-RAY CT SYSTEM AND CONTROL METHOD FOR SAME

CROSS-REFERENCE TO RELATED APPLICATION

This application is based upon and claims the benefit of priority from Japanese Patent Application No. 2009-286444, filed Dec. 17, 2009; the entire contents of which are incorporated herein by reference

FIELD

Embodiments of the present invention relate to an X-ray CT system equipped with a multirow detector (two-dimensional detector).

More specifically, they relate to an X-ray CT system having a configuration to reduce an exposure dose to a subject and a control method thereof.

BACKGROUND

An X-ray CT system is a system that irradiates X-ray beams that are subjected to a rotating operation toward a subject, and forms tomographic images, etc. based on information obtained by detecting X-rays transmitted through the subject. In recent years, as this X-ray CT system, a system provided with a two-dimensional detector has been suggested. A two-dimensional detector has a plurality of rows of detection parts in the rotational axis direction (body axial direction of the subject) of a source that generates beams. Each row of the detection part consists of detection elements aligned in a linear fashion in the rotational direction of the source that generates beams.

Providing a plurality of rows of detection parts in the rotational direction in this way is referred to as multiple detection rows.

In this X-ray CT system equipped with a two-dimensional detector, data over an extensive region of a subject can be acquired by scanning through one rotation. Therefore, in the X-ray CT system using a two-dimensional detector, the number of rotations is small, which is an advantage when attempting to streamline imaging.

By using this X-ray CT system equipped with a two-dimensional detector, multi-slice scanning, volume scanning, dynamic volume scanning, helical scanning in multiple rows, etc., can be performed. Volume scanning is a scanning method in which a whole body is scanned and the data is stored as volume data, and filming, image transfer, etc. can be subsequently performed with respect to the volume data. In addition, the volume data can be divided into a plurality of areas by site to individually designate reconstruction conditions. For example, it is possible to scan from the shoulder to the top of the head at once, and reconstruct an image with a thickness of 10 mm for the top of the head, a thickness of 5 mm for the skull base, and a thickness of 1 mm for the neck. Helical scanning is a method in which X-rays are helically irradiated by rotating a source that generates X-rays and a two-dimensional detector while moving a subject in the body axial direction in order to obtain data. This may cause the source of generating X-rays and the two-dimensional detector to move.

Moreover, when scanning of a region of interest is conventionally performed by performing volume scanning once or a plurality of times, scanning is performed after the number of rows to be used for scanning and the number of times the scan is to be performed are determined such that X-rays are not irradiated to unnecessary regions within the scanning range, with the same number of scanning rows and with the smallest possible number of times the scan is performed (refer to Japanese Unexamined Patent Application Publication No. 2001-59872).

In addition, the subject is exposed to X-ray irradiation, but when this exposure dose is high, the subject is adversely affected.

Therefore, techniques for reducing exposure doses have also been suggested. These techniques include, for example, a Real-EC that calculates the minimum mA with which image display of all slices is possible with the same S/N based on a positioning image, and a Volume EC that calculates the minimum mA from two directions and performs current control such that image display of all slices is possible on the same image from a positioning image, etc.

However, with the conventional method described in Patent Document 1, because a series of scans is performed with the number of rows determined once, the same intensity of X-rays is irradiated to the range for the row width. Therefore, if X-ray irradiance is determined for the purpose of generating an image with good quality, even when there is a part in which exposure to irradiation should be avoided, the X-ray irradiance cannot be reduced only for that part, resulting in higher X-ray irradiance. In addition, when it is intended to reduce irradiation to a part in which exposure to irradiation should be avoided, the X-ray irradiance is also reduced for the surrounding areas of the part in which exposure to irradiation should be avoided, resulting in lower quality of images.

Moreover, although there are techniques to reduce exposure to irradiation such as the Real-EC and the Volume EC as described above, these methods only calculate the dosage of X-rays required to obtain the same quality of images in an entire scanning region, and do not consider parts in which exposure to irradiation should be avoided, such as highly X-ray sensitive parts. In addition, in these methods, the number of rows during scanning is also fixed. Therefore, in these methods as well, the wider the width of the detector in the body axial direction becomes due to multirows, etc., the wider the range in which X-rays are irradiated in one rotation becomes, resulting in scanning sites with different structures in the subject simultaneously; hence, it is difficult to suppress irradiance of X-rays only for parts in which exposure to irradiation should be avoided.

Moreover, with the conventional techniques, in order to perform X-ray irradiation with low X-ray irradiance on regions in which exposure to irradiation should be avoided, it has been necessary to manually set the irradiation fields and the number of rows of detection elements across the entire range of a region of interest, respectively, and doing so is complicated.

DETAILED DESCRIPTION

Embodiments described herein aims to provide an X-ray CT system and a control method for same that are capable of obtaining an irradiation field so as to realize irradiation of X-ray with a desired X-ray irradiance to a region designated within the region of interest, and performing imaging with the irradiation field.

According to embodiments, an X-ray CT system performs scanogram imaging and scanning imaging. The X-ray CT system of embodiments includes the following parts. An X-ray generating part is configured to irradiate X-rays towards a subject. An irradiation field regulating part is configured to variably limit an irradiation field of the X-rays to be irradiated. A detection part is configured to be positioned facing the X-ray generating part across the subject, and have a plurality of rows of detection elements in a body axial direction, in which a plurality of the X-ray detection elements that detect the transmitted X-rays transmitted through the subject is aligned in a direction perpendicular to the body axis of the subject. A moving part is configured to change relative positions between the X-ray generating part, the detection part, and the subject in the body axial direction of the subject. An image generating part is configured to generate image data based on the transmitted X-ray detected by the detection part. A display control part is configured to cause a display part to display an X-ray CT image based on the image data. An imaging region data acquisition part is configured to acquire a first imaging region and a second imaging region that have different widths from each other in the body axial direction of the subject based on the scanogram as imaging regions for performing the scan imaging. An irradiation field control part is configured to obtain an irradiation field for the first imaging region and an irradiation field for the second imaging region, and control the irradiation field regulating part corresponding to the relative positions by the moving part so as to realize the irradiation fields obtained for each the imaging region. An X-ray control part is configured to control the X-ray generating part corresponding to the relative positions by the moving part so as to irradiate X-rays to the first imaging region and the second imaging region for the scan imaging.

(Configuration)

First Embodiment

Figure 1:
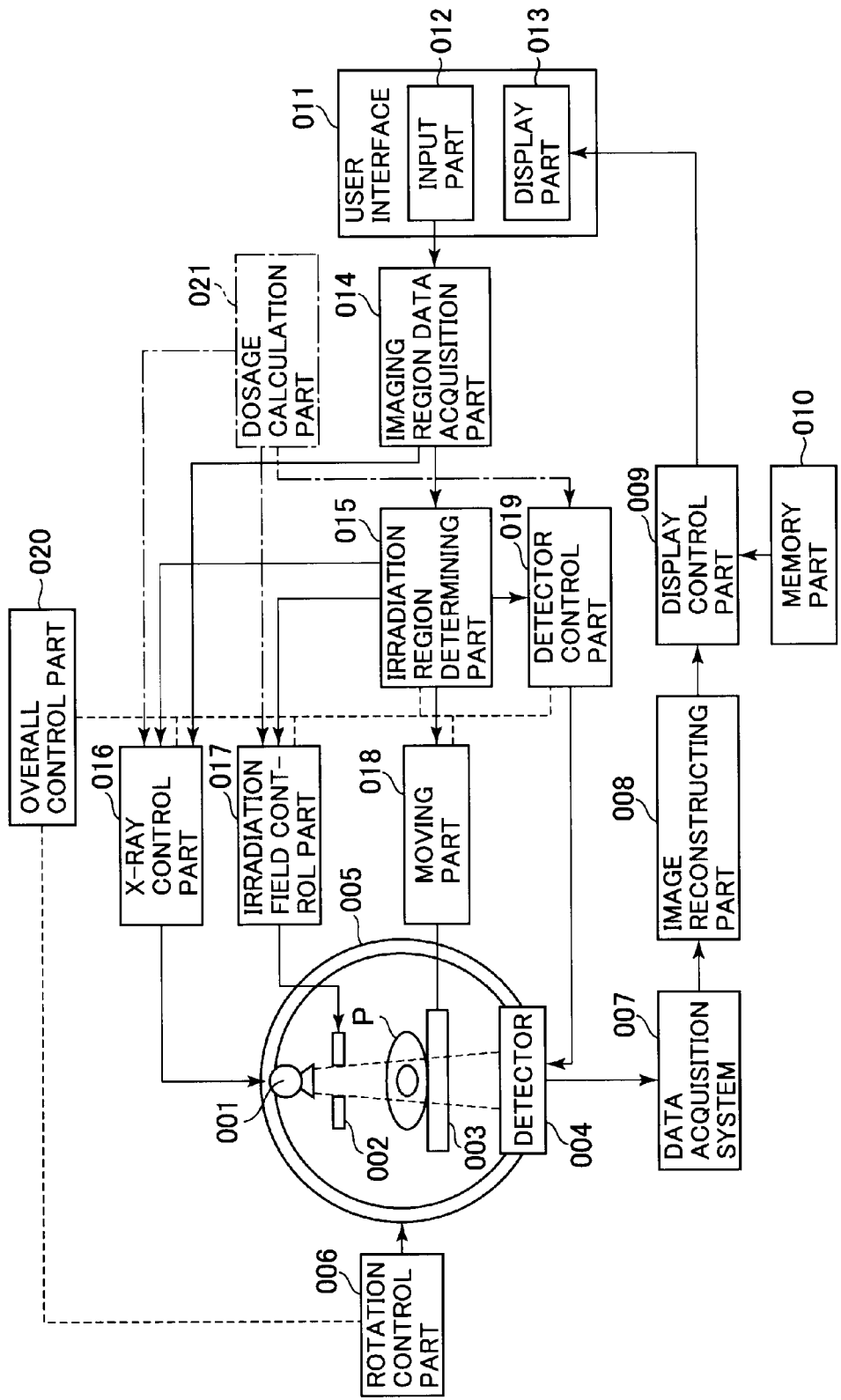
FIG. 1 is a block diagram of the X-ray CT system according to this embodiment.

The X-ray CT system according to a first embodiment will be described below. FIG. 1 is a block diagram showing the functions of the X-ray CT system according to this embodiment. However, in FIG. 1, the parts shown in alternate long and short dash lines are not included in this embodiment, and are described in a second embodiment.

A major configuration for performing imaging with the X-ray CT system is first described below. Subsequently, based on part of a region among imaging regions designated by an operator such as a physician or a laboratory technician (hereinafter simply referred to as "operator"), calculation of each value such as an irradiation field, an X-ray irradiance (also referred to as X-ray dosage), and rows of detectors to be used is described as well as imaging of an X-ray CT image using these calculated irradiation fields, X-ray irradiance, and rows of detectors to be used. An imaging region of a subject to image an X-ray CT image of is referred to as a region of interest (also known as "ROI") below. In addition, the X-ray CT system according to this embodiment has two modes, a scanogram imaging mode and a scanning mode.

The scanogram imaging mode is a mode to perform imaging of a scanogram (an X-ray transparent image for setting an imaging position), and in the X-ray CT system according to this embodiment, for scan planning, imaging of the scanogram is preliminarily performed, and the scanogram is stored in a memory part 010. In imaging of scanogram, an X-ray tube 001 and a detector 004 are fixed, and data collecting operation of X-ray detector data is performed while a bed 003 is linearly moved in the body axial direction of a subject P (hereinafter may be simply referred to as "body axial direction"). Here, the scanogram is generally imaged at view angle positions of 0 degrees and 90 degrees (planar direction and lateral direction). In addition, a scanning mode is a mode to perform imaging of a normal X-ray CT image.

(Major Configuration to Perform Imaging)

The X-ray CT system according to this embodiment has a bed 003 to place a subject P on, and a gantry 005 that rotates around the subject placed on the bed 003 as shown in FIG. 1, and in the gantry 005, an X-ray tube 001 and a detector 004 are positioned facing each other.

In addition, in the gantry 005, a collimator 002 is positioned near an X-ray irradiation opening of the X-ray tube 001.

The X-ray tube 001 is a vacuum tube that generates X-rays, and is provided with the gantry 005. Electric power required to irradiate X-rays is supplied to the X-ray tube 001 through a high voltage generating part (not shown in FIG. 1). The X-ray tube 001 accelerates electrons by the supplied high voltage, and crashes them into a target in order to irradiate X-rays towards the subject P placed within an effective field of view FOV. Moreover, the X-ray tube 001 receives control of an X-ray control part 016 described later, and changes the X-ray irradiance of the X-rays to be irradiated. When the irradiance is high, exposure to irradiation of the subject P is substantial, and when the irradiance is low, exposure to irradiation of the subject P becomes small. This X-ray tube 001 is one example of an "X-ray generating part" or a "X-ray generation source."

The collimator 002, simply described, consists of two plates, and has space between the two plates. Furthermore, the collimator 002 receives control from an irradiation field control part 017 described later, and can change the size of the space by moving the two plates.

The collimator 002 passes X-rays irradiated from the X-ray tube 001 through the space described above so as to irradiate them to the subject P, for example, as pyramid X-ray beams, i.e., corn-beam X-rays.

The collimator 002 then receives control from the irradiation field control part 017 described later and changes the size of the space in order to change the irradiation field of X-rays to be irradiated to the subject P. When the irradiation field is small, the irradiation range (irradiation region) of X-rays to the subject P becomes small, and when the irradiation field is substantial, the irradiation range (irradiation region) of X-rays to the subject P becomes substantial. This collimator 002 is one example of an "irradiation field regulating part."

The detector 004 is positioned facing the X-ray tube 001, and has multi-channel X-ray detection elements to detect X-rays after they are transmitted through the subject P (transmitted X-rays). Here, detecting transmitted X-rays means to detect the X-ray dosage of the transmitted X-rays. Furthermore, this detected X-ray dosage is referred to as "transmitted X-ray data" below. These X-ray detection elements are aligned so as to receive X-ray beams that expand in a direction perpendicular to the body axis of the subject P placed on the bed 003.

This row is referred to as a "row of detection elements" below.

Moreover, in the detector 004 according to this embodiment, a plurality of rows of detection elements is aligned in parallel in the body axial direction of the subject P in accordance with expansion of X-ray beams to be irradiated from the X-ray tube 001 in the body axial direction. For this row of detection elements, for example, 320 rows, etc. are positioned in parallel. As described above, the detector 004 according to this embodiment is a two-dimensional detector (multi-row detector), and the X-ray CT system according to this embodiment is a system capable of volume scanning that implements imaging of a region having a certain width in the body axial direction with one rotation of the gantry 005 described later.

Moreover, the detector 004 receives control from a detector control part 019 described later, and can change the number of rows of detection elements to be used, in other words, rows of detection elements to perform detection of transmitted X-rays transmitted through the subject P. Specifically, for example, when the detector 004 has 320 rows of detection elements, the number of rows of detection elements to be used can be changed, such as using 100 rows of those or using all of the 320 rows. However, in this embodiment, these rows of X-ray elements to be used involve equal number of rows in the body axial direction of the subject P with the center of the aligned rows of detection elements (the center of rows of detection elements in the body axial direction of the subject P) as the center. Specifically, for example, when there are 320 rows, the center is between the 160th row and the 161st row, and predetermined rows in the direction towards the head along the body axis of the subject and in the direction towards the feet along the body axis of the subject therefrom are used. More specifically, when 100 rows are used among the 320 rows, assuming that the number of each row of X-ray elements is from Row 1 to Row 320 in the direction from the head to the feet of the subject, the rows from Row 110 to Row 160 and the rows from Row 161 to Row 210 are used. Change in the number of rows of X-ray elements is determined by the number of rows of detection elements required for an irradiation field of the size determined by the collimator 002; hence, the detector 004 changes it in accordance with the size of the irradiation field of the collimator 002.

The detector 004 detects transmitted X-rays that have been irradiated from the X-ray tube 001, passed the collimator 002, and transmitted through the subject P with each X-ray detection element included in each row of detection elements set to be used. The detector 004 outputs the transmitted X-ray data by transmitted X-rays detected with each X-ray detection element to a data acquisition system 007.

This detector 004 is one example of a "detection part."

The gantry 005 receives control of a rotation control part 006, and performs a rotation around the body axis of the subject P placed on the bed 003. Rotation of the gantry 005 is performed while irradiating X-rays from the X-ray tube 001 described above, and detecting transmitted X-rays by the detector 004.

The data acquisition system 007 has a plurality of DAS (Data Acquisition System) chips (not shown in the figure). The data acquisition system 007 receives input of the transmitted X-ray data in all channels detected by the detector 004. The data acquisition system 007 then performs signal processes such as an amplification process and an A/D conversion process on the transmitted X-ray data that has been input.

The data acquisition system 007 outputs the data subjected to the signal processes to an image reconstructing part 008.

The image reconstructing part 008 receives an input of the data from the data acquisition system 007. The image reconstructing part 008 performs a reconstruction process on the data input from the data acquisition system 007, and generates image data for predetermined slices. Specifically, at the time of scanogram imaging, image data of the scanogram is generated using data of the scanogram (subject transparent data) collected by the data acquisition system 007, and at the time of scanning, image data of an X-ray CT image is generated using the data collected by the data acquisition system 007. The image reconstructing part 008 outputs the generated image data to a display control part 009. These data acquisition system 007 and image reconstructing part 008 are an example of an "image generating part."

The display control part 009 receives an input of the image data from the image reconstructing part 008. The display control part 009 then causes a display part 013 to display the scanogram obtained from the memory part 010, the X-ray CT image based on the image data input from the image reconstructing part 008, various imaging conditions, and an index of a dosage of exposure to irradiation or an exposure dose to the subject by the X-rays, etc. This display control part 009 is one example of a "display control part." In addition, the display part 013 is one example of a "display part."

The memory part 010 consists of a memory medium such as a hard disk. In the memory part 010, the scanogram generated in the image reconstructing part 008 and the image data of the reconstructed X-ray CT image are stored by an overall control part 020.

The overall control part 020 performs mediation for passing data between function parts, and adjustment of operation timing of each function part, etc. However, for convenience of description herein, it may be described as if each function part directly passes data to each other. In addition, the overall control part 020 receives an instruction by an operator to select a mode of either a scanogram imaging mode or a scanning mode from the input part 012, and performs switching of the mode of each function part to the selected mode.

(Calculation of Each Value)

Figure 2:
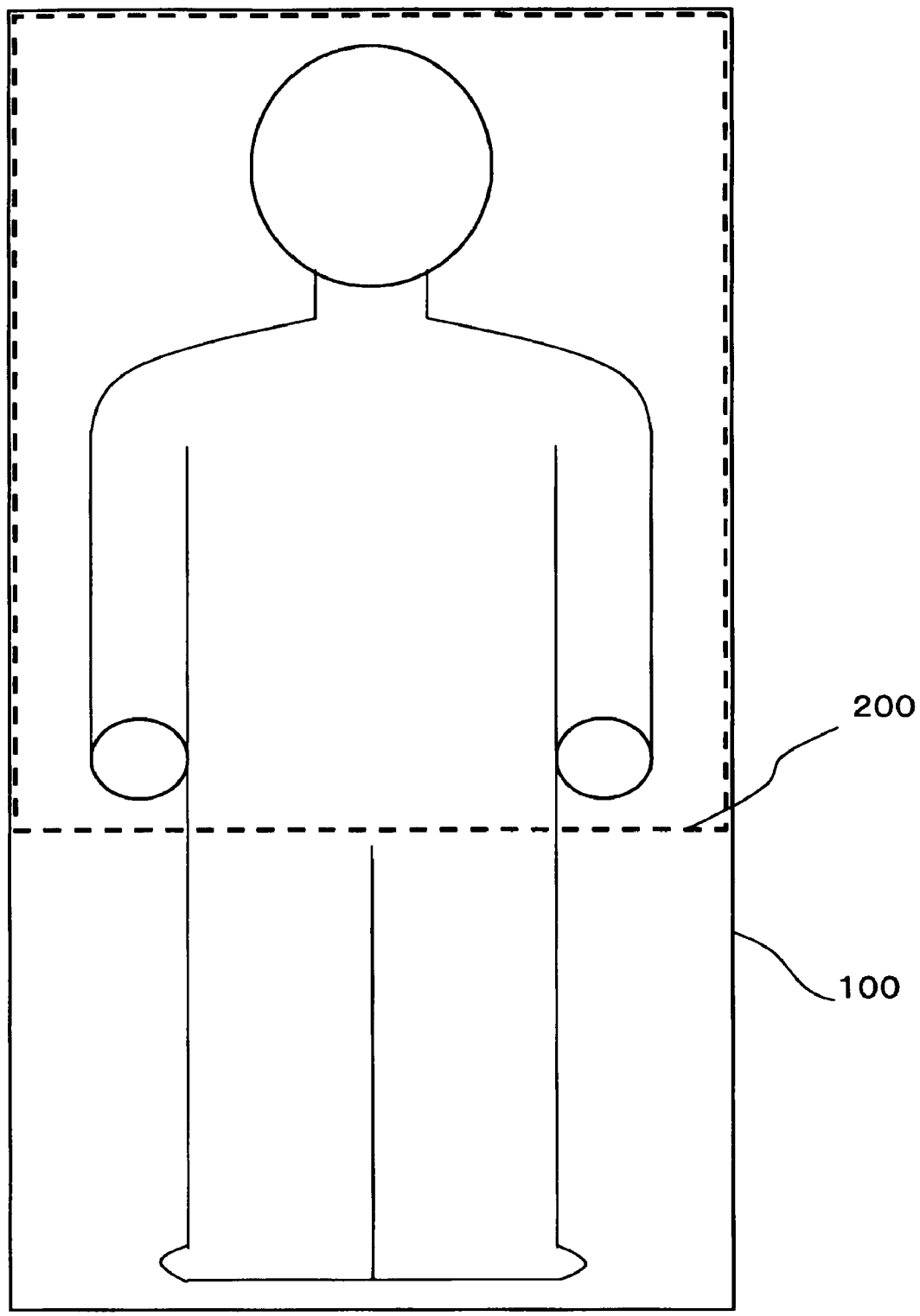
FIG. 2 is a diagram for explaining settings of the region of interest using the scanogram.
Figure 3:
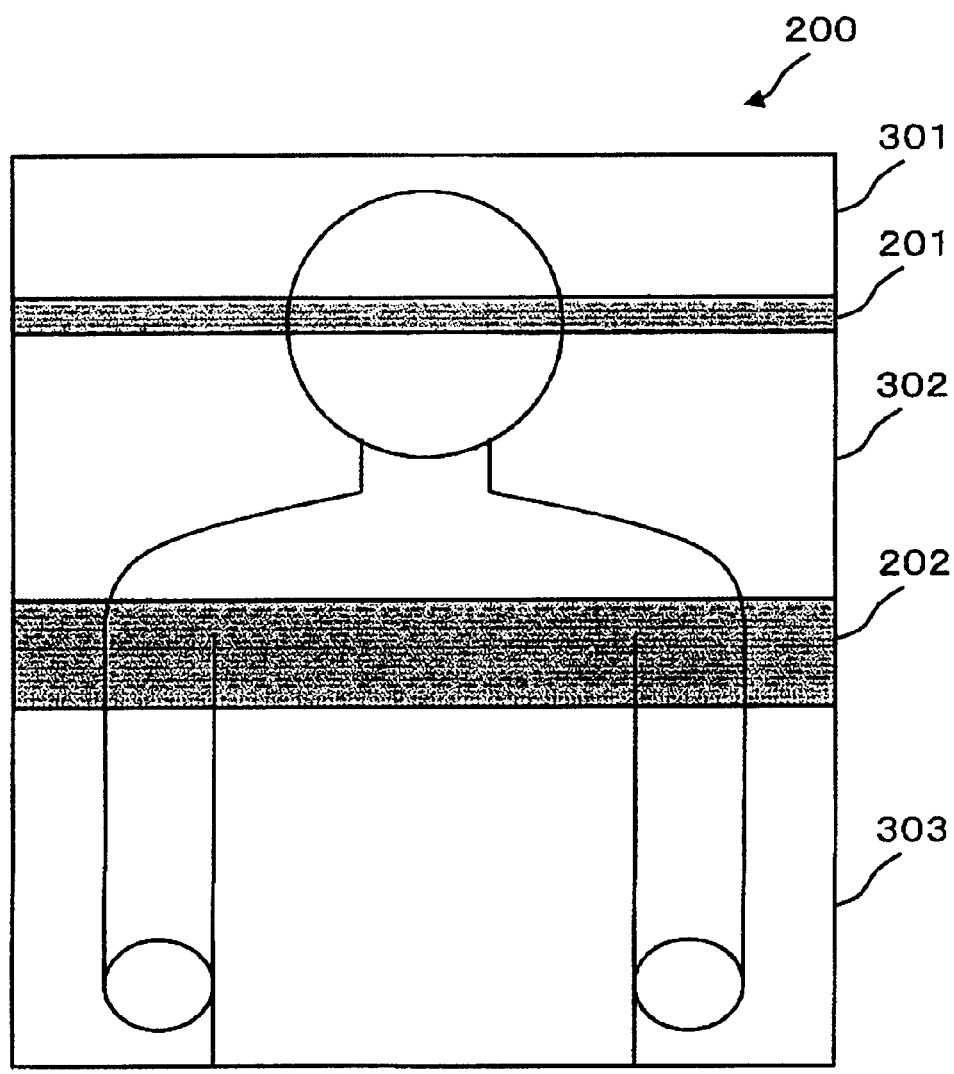
FIG. 3 is a diagram for explaining designation of a partial region within the region of interest (second imaging region).

An operator uses a user interface 011 to designate a region of interest, and designate a partial region included in the region of interest (a region in which X-ray irradiance should be reduced). This part of the region is one example of a "second imaging region." In addition, the region other than the second imaging region of this region of interest is one example of a "first imaging region." Specifically, an operator first inputs a display requirement of scanogram using the input part 012. Based on this requirement, the scanogram 100 shown in FIG. 2 obtained from the memory part 010 is displayed on the display part 013 by the display control part 009. FIG. 2 is a diagram for explaining settings of the region of interest using the scanogram. An operator refers to the scanogram 100 displayed on the display part 013 in order to set the region of interest 200 in which imaging of the subject P is performed using the inputting part 012 such as a mouse (the area surrounded with the dotted line in FIG. 2). Moreover, the operator designates a region 201 and a region 202 that are regions in which X-ray irradiance should be reduced in the region of interest 200 as shown in FIG. 3. FIG. 3 is a diagram for explaining designation of a partial region within the region of interest (second imaging region).

Here, in this embodiment, two regions of the region 201 that is an area of eyes having crystalline lens that are highly X-ray sensitive, and similarly the region 202 that is an area of breasts having mammary glands that are highly X-ray sensitive are designated as regions in which X-ray irradiance should be reduced. However, this region may be one, or three or more. Moreover, the operator inputs X-ray irradiance for the designated region 201 and region 202 (hereinafter referred to as a "second X-ray dosage"), and X-ray irradiance for the regions other than the region 201 and the region 202 of the region of interest 200 (hereinafter referred to as a "first X-ray dosage"). Here, in this embodiment, because irradiation of X-rays at lower X-ray irradiance was used for the region 201 and the region 202 than that for the other regions of the region of interest 200, an operator sets the second X-ray dosage less than the first X-ray dosage. An operator then uses the inputting part 012 to designate the region of interest 200 using this scanogram 100, designates the region 201 and the region 202, and inputs imaging region data including the first and second X-ray dosages corresponding to each region to an imaging region data acquisition part 014.

The imaging region data acquisition part 014 receives the imaging region data from the input part 012. The imaging region data acquisition part 014 then outputs the input imaging region data to the irradiation region determining part 015 and the X-ray control part 016.

This imaging region data acquisition part 014 is one example of "imaging region data acquisition part."

The irradiation region determining part 015 receives the input of the imaging region data from the imaging region data acquisition part 014.

The irradiation region determining part 015 has a memory area such as a memory, and preliminarily stores a width in the body axial direction that can be imaged using the maximum number of rows of detection elements (hereinafter referred to as a "maximum imaging width") in its own memory area. The irradiation region determining part 015, based on the input imaging region data, determines an X-ray irradiation region for each scanning of the respective regions (hereinafter simply referred to as an "irradiation region"). Specifically, the irradiation region determining part 015 refers to the region 201 and the region 202 that are designated regions in the region of interest 200 (second imaging regions) and the region 301, the region 302, and the region 303 that are the other regions (first imaging regions) in order to judge whether or not the width of each region in the body axial direction is larger than the maximum imaging width, and specify regions with a larger width in the body axial direction than the maximum imaging width. In this embodiment, the widths of the region 201, the region 202, and the region 301 in the body axial direction are smaller than the maximum imaging width, and the widths of the region 302 and the region 303 in the body axial direction are larger than the maximum imaging width.

For a region in which the width in the body axial direction is smaller than the maximum imaging width (in this embodiment, the region 201, the region 202, and the region 301), the irradiation region determining part 015 determines a region in which X-rays are irradiated only to that region as an irradiation region.

Figure 4:
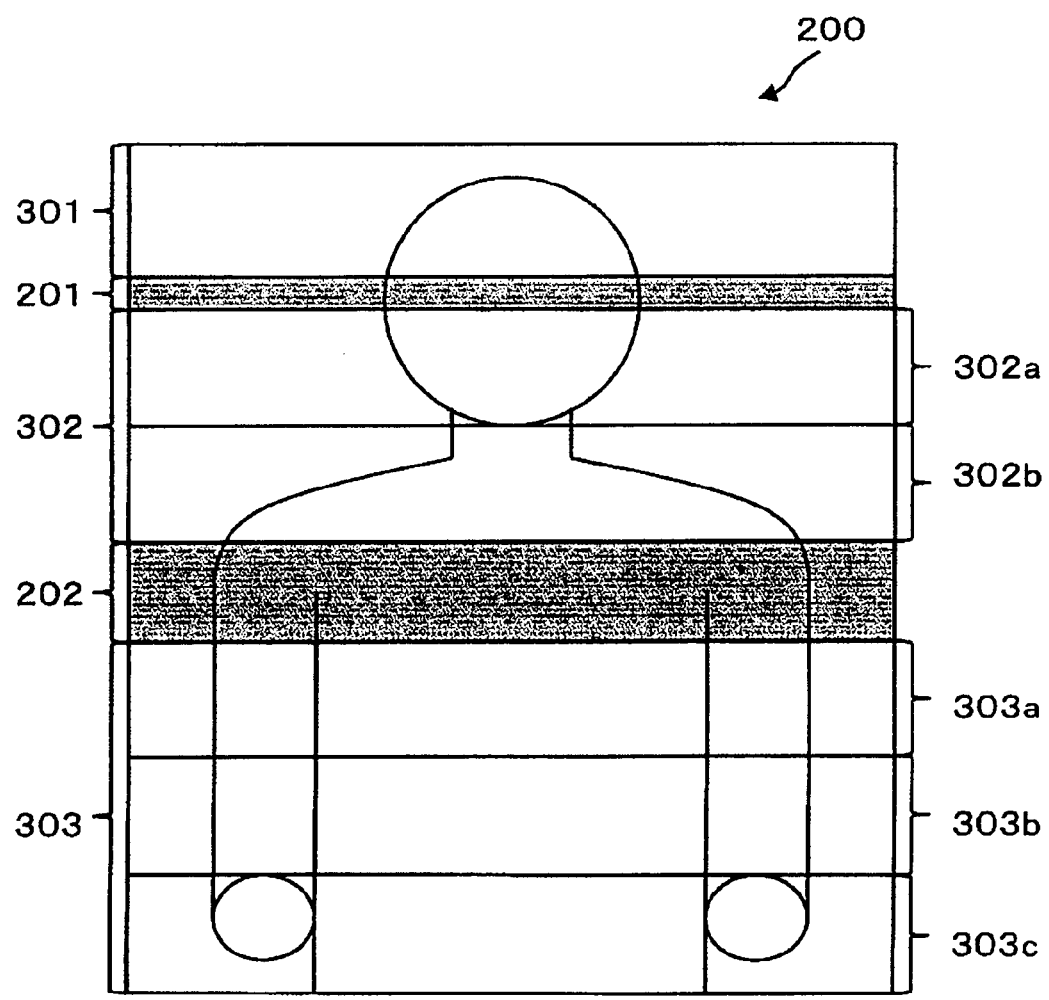
FIG. 4 is a diagram for explaining an example for obtaining irradiation regions based on designation of regions.

In addition, for a region in which the width in the body axial direction is larger than the maximum imaging width (in this embodiment, the region 302 and the region 303), the irradiation region determining part 015 equally divides the region as shown in FIG. 4, and obtains a region that has the maximum width in the body axial direction among widths smaller than the maximum imaging width. Here, FIG. 4 is a diagram for explaining an example for obtaining irradiation regions based on designation of regions. When the width of the region 302 in the body axial direction is divided in half, it becomes smaller than the maximum imaging width; therefore, the irradiation region determining part 015 obtains a region 302a and a region 302b resulted from dividing the region 302 in half in the body axial direction as regions in which irradiation is performed as shown in FIG. 4, and determines the obtained region 302a and the region 302b as irradiation regions. In addition, when the width of the region 303 in the body axial direction is divided into three equal parts, it becomes smaller than the maximum imaging width; therefore, the irradiation region determining part 015 obtains a region 303a, a region 303b, and a region 303c resulted from dividing the region 303 into three equal parts in the body axial direction as regions in which irradiation is performed as shown in FIG. 4, and determines the obtained region 303a, the region 303b, and the region 303c as irradiation regions. Furthermore, the irradiation region determining part 015 outputs the region 301, the region 201, the region 302a, the region 302b, the region 202, the region 303a, region 303b, and the region 303c to the overall control part 020 as irradiation regions. This causes the overall control part 020 to sequentially control a moving part 018 described above such that the center of the rows of detection elements of the detector 004 (i.e., the center of the irradiation field of X-rays in the body axial direction) sequentially conforms to the center of each irradiation region. The state in which the center of the rows of detection elements conforms to the center of each of these irradiation regions is the irradiation position of X-rays for each irradiation region. In the description below, the case in which scanning is performed from the head of the subject P to the feet, i.e., in the order of the region 301, the region 201, the region 302a, the region 302b, the region 202, the region 303a, the region 303b, and the region 303c is explained.

Moreover, the irradiation region determining part 015 outputs the determined irradiation regions to the X-ray control part 016, the irradiation field control part 017, the moving part 018, and the detector control part 019. This irradiation region determining part 015 is one example of an "irradiation region determining part."

The irradiation field control part 017 receives the input of the irradiation regions from the irradiation region determining part 015.

This irradiation field control part 017 is one example of an "irradiation field control part."

The irradiation field control part 017, based on the input irradiation regions, determines irradiation fields for the respective irradiation regions. Specifically, the irradiation field control part 017 obtains an irradiation field for each irradiation region such that X-rays are irradiated only to the respective regions of the region 301, the region 201, the region 302a, the region 302b, the region 202, the region 303a, the region 303b, and the region 303c, which are the irradiation regions that are input with one scanning.

When scanning on the subject P starts, the irradiation field control part 017 receives input of the relative position between the bed 003 and the gantry 005 (i.e., relative positions in the body axial direction of the subject P between the bed 003, the X-ray tube 001, and the detector 004) from the overall control part 020. The irradiation field control part 017 can ascertain which irradiation region of the subject P is irradiated with X-rays based on this relative position between the bed 003 and the gantry 005. Here, in this embodiment, the irradiation field control part 017 receives input of the relative position described above; however, it may be configured to receive other information so long as it can ascertain which irradiation region the gantry 005 is positioned at the irradiation position for, and for example, it may receive input of information from the overall control part 020 such as which irradiation region the next irradiation position or the current irradiation position is a irradiation position for.

When the irradiation position of X-rays input from the overall control part 020 confirms to the region 301, the irradiation field control part 017 controls the collimator 002 to make a change so that the irradiation field will become an irradiation field corresponding to the region 301. Next, when the irradiation position of X-rays input from the overall control part 020 confirms to the region 201, the irradiation field control part 017 controls the collimator 002 to make a change so that the irradiation field will become an irradiation field corresponding to the region 201. As described above, when the irradiation position of X-rays sequentially conforms to each irradiation region, it controls the collimator 002 to change it to an irradiation field corresponding to the irradiation region. However, for convenience of description herein, a change of the irradiation field is made after the irradiation position conforms to each irradiation region, but because it is possible to ascertain which irradiation region X-ray irradiation will be performed next, the irradiation field control part 017 may be configured to control the collimator 002 to make a change to a corresponding irradiation field during the move to the irradiation position at which the next X-ray irradiation is performed.

In addition, in this embodiment, the irradiation region determining part 015 is configured to be a separate function part from the irradiation field control part 017, but this irradiation region determining part 015 may be configured to be included in the irradiation field control part 017.

The X-ray control part 016 receives the input of the imaging region data from the imaging region data acquisition part 014.

Moreover, when scanning the subject P starts, the X-ray control part 016 receives input of the relative position between the bed 003 and the gantry 005 from the overall control part 020.

The X-ray control part 016 refers to the imaging region data, and when the irradiation positions of X-rays are in the regions other than the region 201 and the region 202 in the region of interest 200 (specifically, the region 301, the region 302*a*, the region 302*b*, the region 303*a*, the region 303*b*, and the region 303*c*), it controls the X-ray tube 001 so as to irradiate the first X-ray dosage. In addition, when the irradiation positions of X-rays are in the region 201 and the region 202 within the region of interest 200, the X-ray control part 016 controls the X-ray tube 001 so as to irradiate the second X-ray dosage.

This X-ray control part 016 is one example of an "X-ray control part."

The detector control part 019 receives the input of the imaging region data from the irradiation region determining part 015. This detector control part 019 is one example of a "detector control part."

The detector control part 019 has a memory area such as a memory and preliminarily stores a width in the body axial direction that can be imaged using the maximum number of rows of detection elements (hereinafter referred to as a "maximum imaging width") in its own memory area. The detector control part 019, based on the input imaging region, determines the number of rows of detection elements to be used for the respective regions. Specifically, when X-rays are irradiated only to the respective regions of the region 301, the region 201, the region 302*a*, the region 302*b*, the region 202, the region 303*a*, the region 303*b*, and the region 303*c* with one scanning, the detector control part 019 calculates the number of rows of detection elements required to detect transmitted X-rays through the irradiation field.

When scanning on the subject P starts, the detector control part 019 receives the input of the relative position between the bed 003 and the gantry 005 (i.e., relative positions in the body axial direction between the bed 003, the X-ray tube 001, and the detector 004) from the overall control part 020. Here, in this embodiment, the detector control part 019 receives the input of the relative position described above, but it may be configured to receive other information so long as it can ascertain which irradiation region the gantry 005 is positioned at the irradiation position for, and for example, it may receive input of information from the overall control part 020 such as for which irradiation region the next irradiation position or the current irradiation position is an irradiation position.

When the irradiation position of X-rays input from the overall control part 020 conforms to the region 301, the detector control part 019 controls the detector 004 to make a change such that the number of rows of detection elements to be used becomes a number corresponding to the region 301. Subsequently, when the irradiation position of X-rays input from the overall control part 020 confirms to the region 201, the detector control part 019 controls the detector 004 to make a change such that the number of rows of detection elements to be used becomes an number corresponding to the region 201. As described above, when the irradiation position of X-rays sequentially conforms to each irradiation region, it controls the detector 004 to change the number of rows of detection elements to be used corresponding to the irradiation region. However, for convenience of description herein, a change of the number of rows of detection elements to be used is made after the irradiation position conforms to each irradiation region; however, because it is possible to ascertain for which irradiation region X-ray irradiation is performed next, the detector control part 019 may be configured to control the detector 004 to make a change to a corresponding number of rows of detection elements to be used while it moves to the irradiation position of the next irradiation region.

Here, the detector control part 019 may also be configured with the irradiation region determining part 015 placed thereon in order to obtain an irradiation region along with the irradiation field control part 017, respectively.

The moving part 018 receives a control order from the overall control part 020, and moves the bed 003 in the body axial direction of the subject P. Specifically, the overall control part 020, based on the irradiation region input from the irradiation field control part 017, controls the moving part 018 such that the center of the rows of detection elements of the detector 004 (i.e., the center of the irradiation field of X-rays in the body axial direction) conforms to the center of each irradiation region in the body axial direction.

Specifically, after the overall control part 020 causes the moving part 018 to start moving the bed 003, it obtains the distance of the move of the bed 003 using an encoder, etc. placed on the bed 003, and when it judges, based on the distance, that the irradiation position of X-rays has conformed to each irradiation region, it stops the move of the bed 003 by the moving part 018. The overall control part 020 sequentially performs the move of the bed 003 by the moving part 018 described above for the region 301, the region 201, the region 302*a*, the region 302*b*, the region 202, the region 303*a*, the region 303*b*, and the region 303*c*. This moving part 018 is one example of a "moving part."

The rotation control part 006 receives from the overall control part 020 a notification of completion of the move of the bed 003 to the irradiation position by the moving part 018. After the control of the collimator 002 by the irradiation field control part 017 and the control of the detector 004 by the detector control part 019 are completed, it then rotates the gantry 005 at the irradiation position. This rotation may be performed with the number of rotations preliminarily input by the operator, and for example, the configuration may be used in which the number of rotations preliminarily determined by the operator is input into the imaging region data, the rotation control part 006 refers to the imaging region data, and rotates the gantry 005, etc.

In each irradiation region for the subject P obtained by the irradiation field control part 017, the X-ray CT system according to this embodiment then performs irradiation of X-rays to the subject P by passing it through the irradiation field controlled by the irradiation field control part 017 at the X-ray irradiance controlled by the X-ray control part, detects the transmitted X-rays transmitted through the subject P using the number of rows of detection elements of the detector 004 controlled by the detector control part 019, and generates an X-ray CT image based on the detection results.

(Operation)

Figure 5:
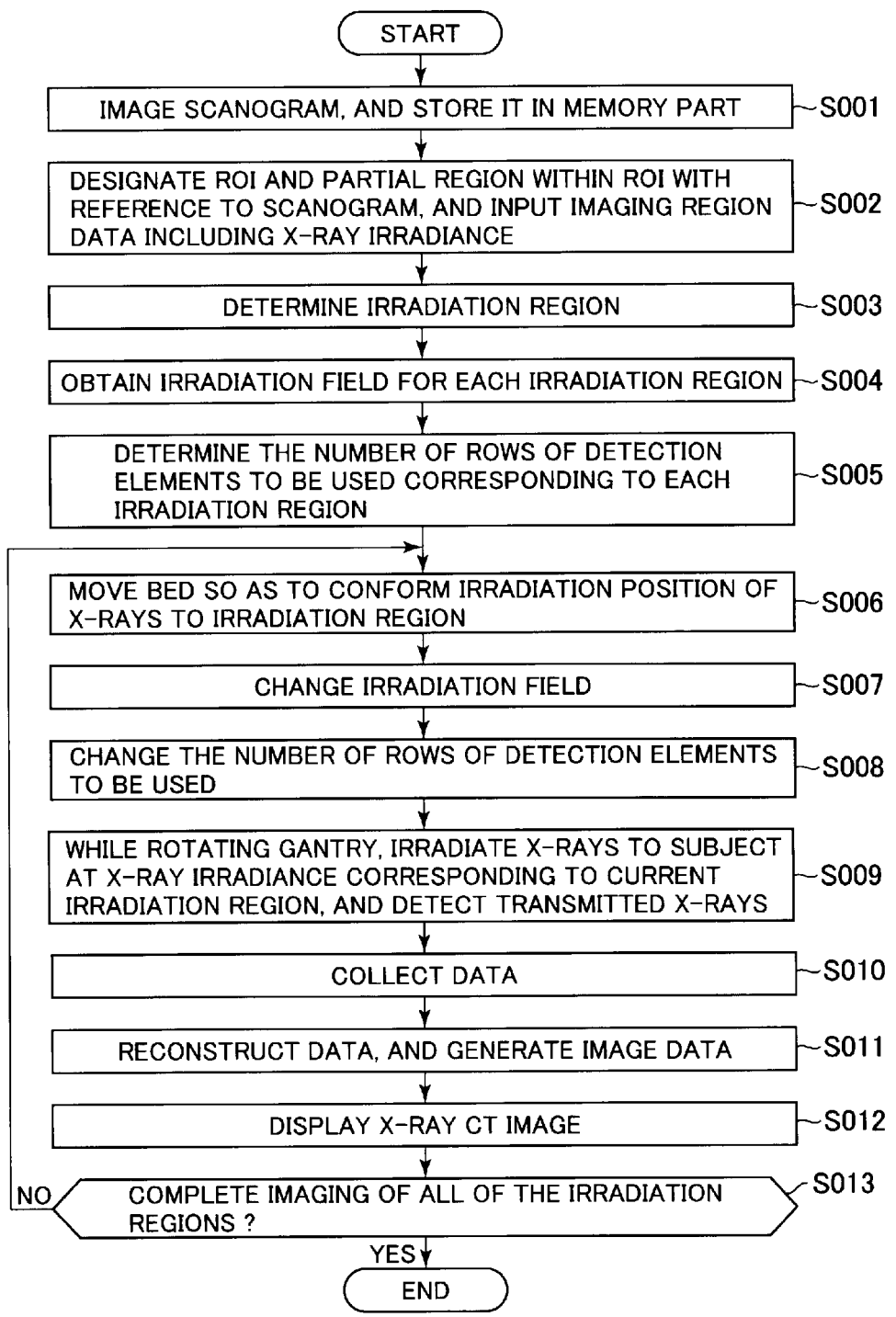
FIG. 5 is a flow chart representing the operation of imaging an X-ray CT image with the X-ray CT system according to this embodiment.

Next, with reference to FIG. 5, the operation of imaging an X-ray CT image with the X-ray CT system according to this embodiment is described. FIG. 5 is a flow chart representing the operation of imaging an X-ray CT image with the X-ray CT system according to this embodiment.

Step S001: The overall control part 020 receives an instruction of scanogram imaging from an operator, performs switching to the scanogram imaging mode, fixes the gantry 005 to a predetermined position, sequentially moves the bed 003 to a predetermined position, irradiates X-rays from the X-ray tube 001, and detects X-rays with the detector 004 in order to image scanogram, and causes the memory part 010 to store the imaged scanogram.

Step S002: An operator uses the user interface 011 to cause the display part 013 to display the scanogram stored in the memory part 010, designates, with reference to the displayed scanogram, a region of interest and a partial region included in the region of interest in which X-ray irradiance should be reduced, using the inputting part 012, further designates X-ray irradiance in each region, and inputs the imaging region data including these designations to the imaging region data acquisition part 014.

Step S003: The irradiation region determining part 015, based on the imaging region data obtained by the imaging region data acquisition part 014, specifies a region in which the width in the body axial direction exceeds the maximum imaging width among the regions designated by an operator and regions other then the designated region, and equally divides the specified region in the body axial direction such that it becomes a region having the maximum width in the body axial direction that is smaller than the maximum imaging width in order to determine an irradiation region. At this time, in the case of a region with the width in the body axial direction being smaller than the maximum imaging width, the region becomes the irradiation region as is.

Step S004: The irradiation field control part 017 obtains an irradiation field for performing scanning for each irradiation region.

Step S005: The detector control part 019 calculates the number of rows of detection elements to be used corresponding to each irradiation region.

Step S006: The overall control part 020, based on the irradiation region input from the irradiation field control part 017, controls the moving part 018 to move the bed 003, and conforms an irradiation position of X-rays to the irradiation region sequentially from the region on the head side of the subject P (the upper region in the drawing of FIG. 4).

Step S007: The irradiation field control part 017 moves the collimator 002, and makes a change such that the irradiation field of X-rays becomes an irradiation field corresponding to the current irradiation region.

Step S008: The detector control part 019 controls the detector 004 to make a change such that the number of rows of detection elements to be used becomes the number of rows of detection elements corresponding to the current irradiation region.

Step S009: The rotation control part 006 rotates the gantry 005. Furthermore, while the gantry 005 is rotating, the X-ray tube 001 irradiates X-rays at X-ray irradiance designated in the imaging region data, and the detector 004 detects transmitted X-rays transmitted through the subject P through the collimator 002.

Step S010: The data acquisition system 007 collects transmitted X-ray data detected with each X-ray detection element of the detector 004, and performs signal processes such as an amplification process and an A/D conversion process.

Step S011: The image reconstruction part 008 reconstructs the data input from the data acquisition system 007, and generates image data.

Step S012: The display control part 009, based on the image data input from the image reconstruction part 008, causes the display part 013 to display an X-ray CT image.

Step S013: The overall control part 020 determines whether or not imaging of all of the irradiation regions input from the irradiation field control part 017 has been completed. When imaging of all of the irradiation regions has not been completed (No), the system returns to Step S006. When imaging of all of the irradiation regions has been completed (Yes), the operation of imaging of the X-ray CT image with the X-ray CT system is completed.

In the flow described above, Step S005 and Step S006 are performed after Step S004; however, this sequence may be reversed or performed simultaneously, and furthermore, the sequence of Step S005 and Step S006 may be reversed or performed simultaneously.

As described above, the X-ray CT system according to this embodiment is configured to receive designations of the region of interest and the partial region thereof, automatically obtains an irradiation region in which X-rays are irradiated only to the designated partial region, and an irradiation regions in which X-rays are irradiated only to the regions other than the designated partial region of the region of interest, performs imaging for the designated partial region at lower X-ray irradiance, and performs imaging for the regions other than the designated partial region in the region of interest at higher X-ray irradiance.

This allows the X-ray CT system according to this embodiment to reduce exposure to irradiation for the region including highly X-ray sensitive parts, which is the designated partial region, by simple operation by an operator and to generate an image with high quality for the other regions. Therefore, it becomes possible to easily reduce exposure to irradiation in parts that do not require high X-ray irradiance, and to provide images with high quality.

In addition, because irradiation regions, in which the width in body axial direction is equal to or less than the maximum imaging width and in which the width is as substantial as possible, are used, examination time can be shortened, and it becomes possible to reduce the burden on the patient.

MODIFIED EXAMPLE

In an X-ray CT system according to this modified example, the method for obtaining an irradiation region differs from the method in the embodiment described previously. Therefore, the method for obtaining an irradiation region by the irradiation region determining part 015 is mainly described below. The block diagram of the X-ray CT system according to this modified example is also the one shown in FIG. 1. In the description below, similarly to the first embodiment, the case in which the region of interest 200 is designated as shown in FIG. 3, and in which the region 201 and the region 202 are designated as partial regions in which X-ray irradiance should be reduced in the region of interest 200, is explained.

Similarly to the embodiment described previously, the irradiation region determining part 015 refers to the imaging region data input from the imaging region data acquisition part 014, and specifies a region in which the width in the body axial direction exceeds the maximum imaging width among the regions designated by an operator, and the regions other than those designated in the region of interest. Here, as the region in which width in the body axial direction exceeds the maximum imaging width, the region 302 and the region 303 in FIG. 3 are specified.

The irradiation region determining part 015 divides the region in which the width in the body axial direction exceeds the maximum imaging width by a region in which the width in the body axial direction is the maximum imaging width, and obtains irradiation regions such that the width of the remaining region becomes smaller than the maximum imaging width. In other words, it divides the original region so as to obtain a plurality of regions in which the width in the body axial direction is the maximum imaging width, and one region having a smaller width than the maximum imaging width.

Figure 6:
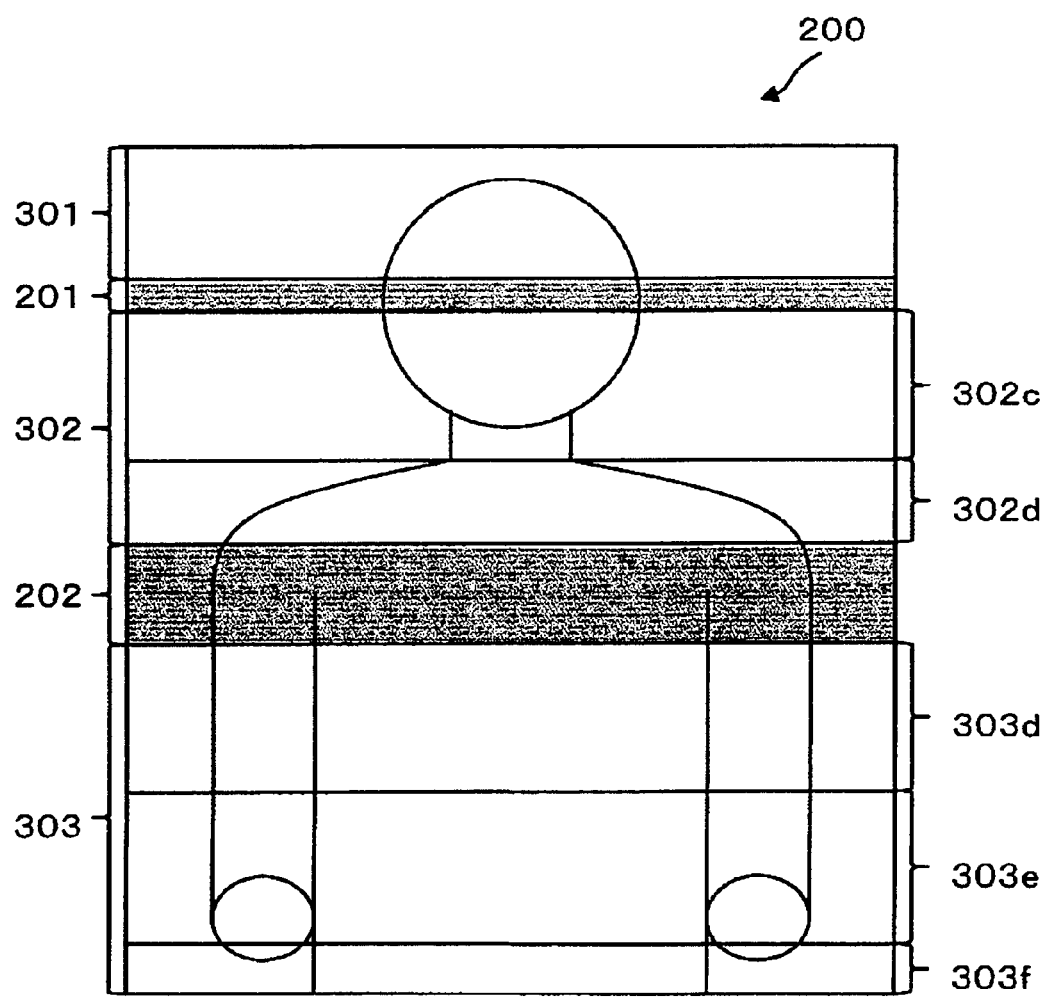
FIG. 6 is a diagram for explaining another example to obtain an irradiation region based on designation of a region.

Specifically, the region 302 and the region 303 are divided as shown in FIG. 6. FIG. 6 is a diagram for explaining another example to obtain an irradiation region based on designation of a region. In other words, the region 302 is divided into a region 302c in which the width in the body axial direction is the maximum imaging width, and a region 302d in which the width in the body axial direction is less than or equal to the maximum imaging width, and the region 303 is divided into a region 303d and a region 303e in each of which the width in the body axial direction is the maximum imaging width, and a region 303f in which the width in the body axial direction is less than or equal to the maximum imaging width.

The irradiation region determining part 015 outputs the obtained irradiation regions to the X-ray control part 016, the irradiation field control part 017, the moving part 018, the detector control part 019, and the overall control part 020.

The irradiation field control part 017 then obtains an irradiation field for each irradiation region.

The detector control part 019 calculates the number of rows of detection elements to be used corresponding to each irradiation region.

Once an order to start scanning is input, the overall control part 020 switches to the scanning mode, and the overall control part 020 controls the moving part 018 to move the bed 003 so as to conform an irradiation position of X-rays to the irradiation region input from the irradiation field control part 017.

Subsequently, X-rays are irradiated at X-ray irradiance corresponding to each irradiation region from the X-ray tube 001 controlled by the X-ray control part 016, and after the data acquisition system 007 collects the transmitted X-ray data detected by the detector 004 and performs signal processes, reconstruction is performed by the image reconstructing part 008, image data is generated, and based on the image data, an X-ray CT image is displayed on the display part 013 by the display control part 009.

In the case that used the method of obtaining an irradiation region as described above, similarly to the embodiment described previously, reduction of exposure to irradiation in parts that do not require high X-ray irradiance and provision of images with high quality can be easily performed, examination time can be shortened, and it becomes possible to reduce a burden on a patient.

In addition, in the first embodiment and the modified example thereof described above, an operator designates a region in the region of interest, in which X-ray irradiance should be reduced; however, in contrast, the configuration may be used in which a region in the region of interest, in which X-ray irradiance should be increased, is designated.

In addition, in the above description, the configuration is that the operator designates a region in the region of interest, in which X-ray irradiance should be reduced, using scanogram; however, for example, the configuration may be used in which designations of the region for the eye part and the region for the breast part are preliminarily input, the region for the eye part and the region for the breast part in the scanogram are automatically detected using an image recognition technique (for example, a method in which approximate positions for the eye part and the breast part are obtained based on the ratio of the entire body), etc., and the regions are automatically set as the designated regions.

In addition, in the above description, the number of rows of detection elements to be used is changed by the detector control part 019; however, this may not be performed. In such case, the method may be used in which all rows of detection elements are used and unnecessary data is deleted later.

In addition, in the above description, the configuration in which the bed 003 is moved has been described; however, the configuration in which the gantry 005 moves in the body axial direction is the same.

Second Embodiment

An X-ray CT system according to a second embodiment is described below. The X-ray CT system according to this embodiment differs from the first embodiment in that it is configured to obtain an irradiation region in accordance with a change in dosage of X-rays required for each part of the subject according to a scanogram.

Therefore, in the explanation below, a method for obtaining an irradiation region is mainly described. The block diagram showing functions of the X-ray CT system according to this example is also shown in FIG. 1. In the description below, the function parts given the same numerals as in the first embodiment have the same functions unless particularly specified.

The X-ray CT system according to this embodiment is configured by adding a dosage calculation part 021 shown in alternate long and short dash lines in FIG. 1 to the first embodiment.

The dosage calculation part 021 has a memory area such as a memory. Moreover, the dosage calculation part 021 has statistical data in its own memory area, that when X-ray irradiation was previously performed, at what degree of X-ray irradiance, and to which position of the subject the irradiation of X-rays was performed.

Figure 7:
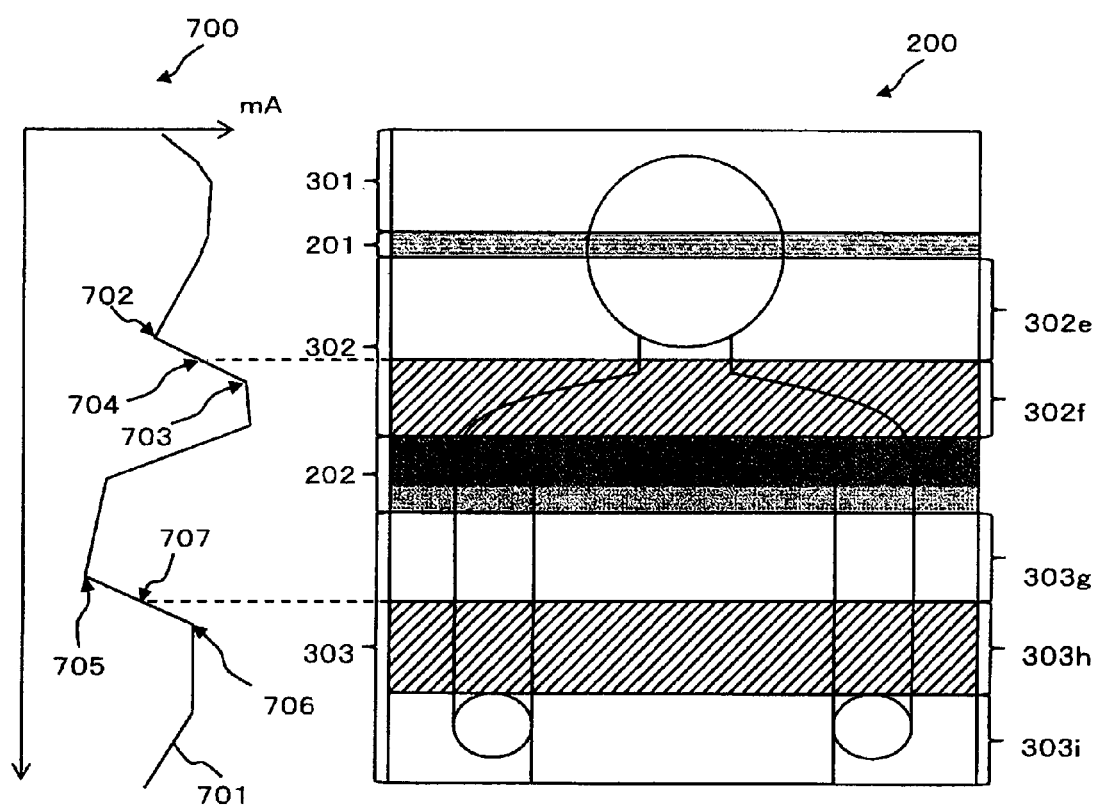
FIG. 7 is a diagram for explaining one example to obtain an irradiation region based on X-ray irradiance required at each point in the body axial direction.

The dosage calculation part 021 then obtains a scanogram from the memory part 010, calculates, based on the statistical data stored in itself, what degree of X-ray irradiance is required for which part in the body axial direction of the subject imaged in the scanogram, and creates a graph 700 shown in FIG. 7. The graph 700 is a graph with the horizontal axis as X-ray irradiance (mA) and the vertical axis as positions in the body axial direction of scanogram. Here, FIG. 7 is a diagram for explaining one example to obtain an irradiation region based on X-ray irradiance required at each point in the body axial direction. A curve 701 of the graph 700 represents values of X-ray irradiance to be used that has been statistically obtained for a position in the body axial direction of the subject P. The dosage calculation part 021 outputs the created graph 700 to the irradiation field control part 017 and the detector control part 019. Creation of the graph 700 and output to the irradiation region determining part 015 by this dosage calculation part 021 are preliminarily performed prior to actual imaging (scanning), and the irradiation region determining part 015 has preliminarily stored this graph 700 prior to actual imaging (scanning).

The irradiation region determining part 015 has preliminarily stored a threshold level of an amount of change in the curve 701. In addition, as described above, the irradiation region determining part 015 has preliminarily stored the graph 700. The threshold level of an amount of change is a threshold level for a differential value at each point of the curve 701. In other words, the irradiation field control part 017 differentiates the curve 701 at its each point to obtain a differential value, and when the differential value exceeds the threshold level that is preliminarily stored, it judges that the amount of change is substantial.

The irradiation region determining part 015 then makes a cut for an irradiation region at a position that is the center of the position of a point in the body axial direction at which the continuous amount of change in the curve 701 exceeds the threshold level. However, when a point at which the amount of change exceeds the threshold level is included in the designated region (here, the region 201 and the region 202), the irradiation region determining part 015 does not make a cut for an irradiation region at that position. The irradiation region determining part 015 then obtains the width in the body axial direction from where a cut is made at the point with a substantial amount of change to where a cut is made at the next point with a substantial amount of change, or to a designated region, and when the obtained width is equal to or smaller than the maximum imaging width, the region is treated as an irradiation region as is, and when the obtained width is larger than the maximum imaging width, it obtains the region in which the width in the body axial direction between the cuts has been equally divided as an irradiation region.

Here, in this embodiment, a cut for an irradiation region has been made at the position that is the center of a point in the body axial direction at which the continuous amount of change exceeds the threshold; however, another point may be used for this, and for example, the center of gravity of the continuous points may be obtained, and the position of the point in the body axial direction may be considered as a cut for an irradiation region.

In addition, as the position of a cut for this irradiation region, the configuration may be used in which a range that does not exceed the threshold level of an amount of change is considered as an irradiation region with a peak portion or the center of gravity of X-ray irradiance as the center.

In this embodiment, as shown in FIG. 7, continuous points at which an amount of change exceeds the threshold level are from a point 702 to a point 703, and from a point 705 to a point 706.

Therefore, the irradiation region determining part 015 makes cuts for regions at positions of the point 704 that is the center in the body axial direction between the point 702 and the point 703, and at position of the point 707 that is the center in the body axial direction between the point 705 and the point 706. Here, the amount of change at the point of the curve 701 at the position corresponding to the region 202 also exceeds the threshold level; however, because this is included in the designated region as described above, a cut is not made. Here, the region from the designated region 201 to the position of the point 704 in the body axial direction, the region from the position of the point 704 in the body axial direction to the region 202, and the region from the designated region 202 to the position of the point 707 in the body axial direction have less than or equal to the maximum imaging width, respectively, and they are a region 302*e*, a region 302*f*, and a region 303*g* that are irradiation regions, respectively. Moreover, there are no points from the position of the point 707 in the body axial direction to the end of the region of interest 200, in which the amount of change exceeds the threshold level, and the width in the body axial direction in between exceeds the maximum imaging width; therefore, the irradiation field control part 017 equally divides the region from the position of the point 707 in the body axial direction to the end of the region of interest 200 in the body axial direction in order to obtain a region 303*h* and a region 303*i*. Moreover, because there are no points in which the amount of change exceeds the threshold level in the region 301, and it does not exceed the maximum imaging width; hence, the irradiation field control part 017 considers it as an irradiation region as is. In addition, because the region 201 and the region 202 are designated regions, and they do not exceed the maximum imaging width, the irradiation field control part 017 considers them as irradiation regions as is.

The irradiation region determining part 015 then outputs the obtained irradiation regions to the X-ray control part 016, the irradiation field control part 017, the moving part 018, the detector control part 019, and the overall control part 020.

The irradiation field control part 017 obtains irradiation fields corresponding to the input irradiation regions.

The detector control part 019 calculates the number of rows of detection elements to be used corresponding to the input irradiation regions.

The X-ray control part 016 receives an input of the irradiation regions from the overall control part 020. Furthermore, the X-ray control part 016 receives an input of the graph 700 from the dosage calculation part 021. It then controls the X-ray tube 001 with the maximum X-ray irradiance in each irradiation region as the X-ray irradiance in the irradiation region. Here, another value may be selected for the X-ray irradiance in each irradiation region, and for example, it may be a mean value of X-ray irradiance at each point of the irradiation region in the body axial direction, etc.

Each function part then performs irradiation and detection of X-rays in accordance with the move of the bed 003 by the moving part 018 under control of the overall control part 020, using the set irradiation fields, the calculated rows of detection elements to be used, and the X-ray irradiance that correspond to each irradiation region, generates image data using the detected data, and causes the display part 013 to display.

As described above, the X-ray CT system according to this embodiment is configured to use irradiation regions divided at parts in which required X-ray irradiance extremely changes for imaging based on X-ray irradiance at each position of the subject P in the body axial direction that has been statistically calculated.

This allows for performing irradiation of X-rays at low X-ray irradiance only for parts in which exposure to irradiation should be avoided, and allows it to avoid irradiating X-rays at high X-ray irradiance for parts in which required X-ray irradiance is low.

Therefore, it becomes possible to reduce damage of exposure to irradiation to a patient.

MODIFIED EXAMPLE

An X-ray CT system according to this modified example differs from the embodiment described previously in that it is configured to suppress X-ray irradiation to parts in which exposure to irradiation should be avoided by further dividing an irradiation region when the parts in which exposure to irradiation should be avoided are irradiated at high X-ray irradiance, taking a cone angle of X-rays (expansion of X-ray beams in the body axial direction) into consideration. Therefore, the method for obtaining an irradiation region by the irradiation field control part 017 is mainly described below. The block diagram of the X-ray CT system according to this modified example is also shown in FIG. 1.

The irradiation region determining part 015 according to this modified example has stored a threshold of an irradiation angle of X-rays. Here, a cone angle of X-rays is described. X-rays irradiated from the X-ray tube 001 are irradiated to the subject P through the collimator 002; however, at this time, the X-rays are irradiated to the subject P while expanding. In the X-rays irradiated at this time, an expansion angle in the body axial direction is a cone angle. The end portion of these irradiated X-rays is not used for image formation; however, when an image of an irradiation region is imaged, the end portion of the X-rays hits outside the irradiation region. Moreover, the larger an irradiation field in the body axial direction is, the larger the cone angle corresponding thereto becomes, and the ratio of the X-rays being irradiated to parts other than the irradiation region becomes high.

Therefore, the irradiation field control part 017 divides the irradiation field into smaller parts such that X-rays are not applied outside the irradiation region, and creates irradiation regions in which the cone angles corresponding to the irradiation fields divided into smaller parts are made small.

The method for obtaining this irradiation region is described in more detail. First, the irradiation region determining part 015 obtains an irradiation region similarly to the embodiment described previously.

Here, because a cone angle is determined according to the size of the irradiation region, the irradiation region determining part 015 can ascertain the cone angle at the time point of determining the irradiation region. Specifically, in the case in which each of the irradiation region 302*a* and the irradiation region 302*b* (see FIG. 4) are obtained by equally dividing the irradiation region 302 (see FIG. 3), when X-rays are irradiated to each of the irradiation regions 302*a* and 302*b* with a cone angle corresponding thereto, and when the end portion of the X-rays is applied outside the irradiation regions 302*a* and 302*b* (that is, the irradiation region 201 or the irradiation region 202 shown in FIG. 4), the irradiation region determining part 015 obtains irradiation regions which are divided smaller so as to reduce the area outside the irradiation region to which the end portion of the X-rays are applied (that is, the number of division of the irradiation region is increased, such as adopting division into three equal regions instead of division in half), and determines the size of the cone angle in accordance with the obtained irradiation regions.

On the other hand, in the case in which the irradiation region 301 is not equally divided as shown in FIG. 3, FIG. 4 and FIG. 7, when X-rays are irradiated with a cone angle corresponding to the irradiation regions 301, and when the end portion of the X-rays is applied outside the irradiation regions 301 (for example, the irradiation region 201 shown in FIG. 3 etc.), the irradiation region determining part 015 equally divides the region 301, obtains irradiation regions which are divided so as to reduce the area outside the irradiation region 301 to which the end portion of the X-rays are applied, (that is, increases the number of division of the irradiation region), and determines the size of the cone angle in accordance with the obtained irradiation regions.

Here, in this embodiment, by increasing the number of regions equally divided, when X-rays are irradiated to the irradiation regions, the end portion of the X-rays is not applied outside the irradiation regions; however, another method may be used so long as irradiation is not performed much during X-ray irradiance of other irradiation regions for parts in which exposure to irradiation should be avoided.

For example, the method may be used in which a cone angle corresponding to an irradiation region adjacent to a region in which exposure to irradiation should be avoided is adjusted, and the remaining part that is not adjacent to the region in which exposure to irradiation should be avoided is considered as an irradiation region as is, or is equally divided and considered as irradiation regions.

Based on these obtained irradiation regions, each function part performs irradiation and detection of X-rays in accordance with the move of the bed 003 by the moving part 018 under control of the overall control part 020, using the obtained irradiation fields, the calculated rows of detection elements to be used, and the X-ray irradiance that correspond to each irradiation region, generates image data using the detected data, and causes the display part 013 to display.

As described above, the X-ray CT system according to this modified example is configured to further divide an irradiation region when irradiation is performed to parts in which exposure to irradiation should be avoided at high X-ray irradiance, taking a cone angle of X-rays into consideration.

This allows for suppressing irradiation of excessive X-rays to parts in which exposure to irradiation should be more reduced, and it becomes possible to further reduce damage from exposure to irradiation of a patient.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT system that performs scanogram imaging and scanning imaging, comprising:
    an X-ray generating part configured to irradiate X-rays towards a subject;
    an irradiation field regulating part configured to variably limit an irradiation field of said X-rays to be irradiated;
    a detection part configured to be positioned facing said X-ray generating part across said subject, and have a plurality of rows of detection elements in a body axial direction, in which a plurality of the X-ray detection elements that detect the transmitted X-rays transmitted through said subject is aligned in a direction perpendicular to the body axis of said subject;
    a moving part configured to change relative positions between said X-ray generating part, said detection part, and said subject in the body axial direction of said subject;

an image generating part configured to generate image data based on said transmitted X-ray detected by said detection part; and a display control part configured to cause a display part to display an X-ray CT image based on said image data; and the X-ray CT system comprising:

an imaging region data acquisition part configured to acquire a first imaging region and a second imaging region that have different widths from each other in the body axial direction of said subject based on said scanogram as imaging regions for performing said scan imaging;

an irradiation field control part configured to obtain an irradiation field for said first imaging region and an irradiation field for said second imaging region, and control said irradiation field regulating part corresponding to said relative positions by said moving part so as to realize said irradiation fields obtained for each said imaging region; and an X-ray control part configured to control said X-ray generating part corresponding to said relative positions by said moving part so as to irradiate X-rays to said first imaging region and said second imaging region for said scan imaging.

2. The X-ray CT system according to claim 1, further comprising an inputting part, wherein said second imaging region is a region that is designated either by operating said inputting part or by recognizing the image of said scanogram.

3. The X-ray CT system according to claim 1, wherein said X-ray control part is configured to control said X-ray generating part so as to irradiate X-rays with a first X-ray dosage and a second X-ray dosage that are different from each other for said first imaging region and said second imaging region.

4. The X-ray CT system according to claim 1, further comprising:

an irradiation region determining part configured to, when each of said first imaging region and said second imaging region is larger than the maximum imaging width in said body axial direction imageable based on the maximum number of rows of said rows of detection elements, divide it into imaging regions smaller than said maximum imaging width, and determines X-ray irradiation regions for each said scan imaging, wherein said irradiation field control part is configured to obtain, based on said X-ray irradiation regions obtained by said irradiation region determining part, irradiation fields to be used for imaging of each of the X-ray irradiation regions, and control said irradiation field regulating part so as to realize said irradiation fields obtained for each of said X-ray irradiation regions.

5. The X-ray CT system according to claim 4, further comprising:

a detector control part configured to, based on said X-ray irradiation region obtained by irradiation region determining part, calculate the number of said rows of detection elements to be used for imaging of said each X-ray irradiation region, and control said detection part so as to use the number of said rows of detection elements calculated for said each X-ray irradiation region at the time of said scan imaging corresponding to said relative positions by said moving part.

6. The X-ray CT system according to claim 4 or 5, wherein said irradiation region determining part is configured to, when any of said first imaging region and said second imaging region is a large imaging region having a larger width in said body axial direction than said maximum imaging width, equally divide said large imaging region in said body axial direction in order to make regions less than said maximum imaging width, and obtain irradiation fields corresponding to said equally divided regions.

7. The X-ray CT system according to claim 4 or 5, wherein said irradiation region determining part is configured to, when any of said first imaging region and said second imaging region is a large imaging region having a larger width in said body axial direction than said maximum imaging width, divide said large imaging region into one region or a plurality of regions having said maximum imaging width and a remaining region, and obtain irradiation fields corresponding to said divided regions.

8. The X-ray CT system according to claim 4, comprising a graph that indicates X-ray irradiance at each position along said body axial direction of said subject in all of said imaging regions, wherein said irradiation region determining part is configured to divide all of said imaging regions at a position calculated based on a position in said body axial direction that has a large amount of change in said graph, and obtains irradiation fields corresponding to said divided regions.

9. The X-ray CT system according to claim 8, wherein said irradiation region determining part is configured to, when X-rays are irradiated to the obtained irradiation field at a cone angle corresponding to said obtained irradiation field, and when said X-rays are irradiated to an irradiation field adjacent to said irradiation field, divide said obtained irradiation field such that said X-rays are not irradiated to said adjacent irradiation field.

10. The X-ray CT system according to any one of claims 1 to 5, wherein said second X-ray dosage is less than said first X-ray dosage.

11. A control method of an X-ray CT system that performs scanogram imaging and scan imaging, comprising:

an X-ray generation source configured to irradiate X-rays towards a subject;

a collimator configured to variably limit an irradiation field of said X-rays that have been irradiated;

a detector configured to be positioned facing said X-ray generation source across said subject, and have a plurality of rows of detection elements in a body axial direction, in which a plurality of the X-ray detection elements that detect the transmitted X-rays transmitted through said subject is aligned in the direction perpendicular to the body axis of said subject;

a moving mechanism configured to relatively move the X-ray generation source, the detector, and said subject in the body axial direction of said subject; and an image generating part configured to generate image data based on said transmitted X-ray detected by said detector; and the control method of an X-ray CT system comprising:

a step to perform scanogram imaging;

an imaging region data acquisition step to acquire imaging region data, in which the entire imaging region of said subject has been sectionalized in the body axial direction based on said scanogram into a first imaging region to be imaged with a first X-ray dosage, and a second imaging region with a second X-ray dosage less than the first X-ray dosage, and has been so designated;

an irradiation region determining step to divide said first imaging region and said second imaging region into imaging regions of widths smaller than the maximum imaging width in said body axial direction imageable using the maximum number of rows of said rows of detection elements, and determine a plurality of X-ray irradiation regions;

an irradiation field calculating step to obtain respective irradiation fields for performing irradiation of X-rays to each of said X-ray irradiation regions;
a moving step to relatively move the X-ray generation source, the detector, and said subject in the body axial direction of said subject;
an irradiation field control step to control said collimator corresponding to said relative position so as to realize said obtained irradiation fields corresponding to each said X-ray irradiation region;
an X-ray dosage control step to control X-ray irradiance of said X-ray generation source corresponding to said relative positions so as to irradiate said first X-ray dosage to said first imaging region, and irradiate said second X-ray dosage to said second imaging region;
an X-ray irradiating step to irradiate X-rays towards said subject;
an X-ray detecting step to detect the transmitted X-ray irradiated and transmitted through said subject;
an image data generating step to generate image data based on said transmitted X-ray that has been detected; and
an image display control step to cause a display part to display an X-ray CT image based on said image data.

* * * * *